United States Patent
Comor et al.

(10) Patent No.: US 11,594,345 B2
(45) Date of Patent: Feb. 28, 2023

(54) METHOD FOR PRODUCING AC-225 FROM RA-226

(71) Applicant: Ion Beam Applications, Louvain-la-Neuve (BE)

(72) Inventors: Jozef Comor, Louvain-la-Neuve (BE); Jean-Michel Geets, Louvain-la-Neuve (BE); Gerd-Jürgen Beyer, Louvain-la-Neuve (BE)

(73) Assignee: Ion Beam Applications, Louvain-la-Neuve (BE)

( * ) Notice: Subject to any disclaimer, the term of this patent is extended or adjusted under 35 U.S.C. 154(b) by 114 days.

(21) Appl. No.: 17/104,185

(22) Filed: Nov. 25, 2020

(65) Prior Publication Data

US 2021/0210245 A1 Jul. 8, 2021

(30) Foreign Application Priority Data

Nov. 29, 2019 (EP) .................................... 19212438

(51) Int. Cl.
 *G21G 1/00* (2006.01)
 *G21G 1/12* (2006.01)
 (Continued)

(52) U.S. Cl.
 CPC .............. *G21G 1/12* (2013.01); *G21G 4/04* (2013.01); *A61K 51/00* (2013.01); *B25J 21/02* (2013.01);
 (Continued)

(58) Field of Classification Search
 CPC ... G21G 4/04; G21G 4/08; C25D 3/54; A61K 51/00; C25C 1/00; C01B 2203/1064; G21F 7/04; B25J 21/02
 See application file for complete search history.

(56) References Cited

U.S. PATENT DOCUMENTS

| | | | | |
|---|---|---|---|---|
| 5,809,394 A | * | 9/1998 | Bray | G21G 4/00 423/3 |
| 6,680,993 B2 | * | 1/2004 | Satz | G21G 1/10 376/105 |

(Continued)

FOREIGN PATENT DOCUMENTS

| | | | |
|---|---|---|---|
| CN | 109468665 A | * | 3/2019 |
| EP | 0752710 A1 | | 1/1997 |

(Continued)

OTHER PUBLICATIONS

Rane, Arvind T., and Kashinath S. Bhatki. "Electrodeposition of carrier-free manganese-54, technetium-99 and actinium-288 from aqueous baths." The International Journal of Applied Radiation and Isotopes 24.7 (1973): 385-389. (Year: 1973).*

(Continued)

*Primary Examiner* — Lily C Garner
(74) *Attorney, Agent, or Firm* — Finnegan, Henderson, Farabow, Garrett & Dunner, LLP

(57) ABSTRACT

The embodiments of the present disclosure provide a method for producing Ac-225 from Ra-226, comprising submitting Ra-226 to a photo-nuclear process, collecting an electrochemical precipitation of an Ac-225 on a cathode in a recipient, removing the cathode from the recipient after the electrochemical precipitation of the Ac-225, transferring the cathode to a hot cell environment, and extracting the Ac-225 from the cathode in the hot cell environment. The Ra-226 may comprise a liquid solution in the recipient, and submitting Ra-226 to the photo-nuclear process may comprise irradiating the Ra-226 to produce Ra-225. The Ra-225 may decay into Ac-225 upon irradiation of the Ra-226.

11 Claims, 2 Drawing Sheets

(51) Int. Cl.
*G21G 4/04* (2006.01)
*G21F 7/04* (2006.01)
*C25C 1/00* (2006.01)
*C25C 1/22* (2006.01)
*H05H 6/00* (2006.01)
*A61K 51/00* (2006.01)
*B25J 21/02* (2006.01)

(52) U.S. Cl.
CPC .................. *C25C 1/00* (2013.01); *C25C 1/22* (2013.01); *G21F 7/04* (2013.01); *G21G 2001/0089* (2013.01); *H05H 6/00* (2013.01)

(56) References Cited

U.S. PATENT DOCUMENTS

| | | | |
|---|---|---|---|
| 6,793,799 B2* | 9/2004 | Ozawa | C25C 1/00 205/559 |
| 8,349,391 B2 | 1/2013 | Harfensteller | A61K 51/1282 427/5 |
| 9,202,600 B2* | 12/2015 | Ravn | G21G 1/001 |
| 9,790,573 B2* | 10/2017 | Moreno Bermudez | C22B 7/005 |
| 10,882,196 B2 | 1/2021 | Scotchmer | B23K 9/325 |
| 10,930,407 B2* | 2/2021 | Sandquist | G21G 1/06 |
| 2002/0094056 A1* | 7/2002 | Satz | G21G 1/10 376/215 |
| 2003/0099322 A1* | 5/2003 | Ozawa | C01B 3/042 376/324 |
| 2003/0164300 A1* | 9/2003 | Pernel | C25C 3/34 205/43 |
| 2007/0076834 A1* | 4/2007 | Moreno Bermudez | A61K 51/1282 376/194 |
| 2008/0152078 A1* | 6/2008 | De Sanoit | G21G 4/06 378/44 |
| 2009/0162278 A1 | 6/2009 | Ravn et al. | |
| 2009/0191122 A1* | 7/2009 | Moreno Bermudez | G21G 4/08 424/1.61 |
| 2016/0148712 A1* | 5/2016 | Sandquist | G21G 1/06 376/158 |

FOREIGN PATENT DOCUMENTS

| | | | | |
|---|---|---|---|---|
| EP | 0752710 B1 * | 11/1999 | | A61K 51/1282 |
| WO | WO 01/41154 A1 | 6/2001 | | |
| WO | WO-2020260210 A1 * | 12/2020 | | G21G 1/10 |
| WO | WO-2021002275 A1 * | 1/2021 | | A61K 33/244 |

OTHER PUBLICATIONS

European Search Report for International Application No. EP 19212438.6 from the European Patent Office, dated May 25, 2020 (5 pages).
Rose A. Boll, et al., "Production of actinium-225 for alpha particle mediated radioimmunotherapy," Applied Radiation and Isotopes 62 (2005), pp. 667-679 (2005).
David A. Sheinberg, et al., "Actinium-225 in targeted alpha-particle therapeutic applications," Curr Radiopharm 4(4), pp. 306-320 (2011).
B. L. Zhuikov, et al., "Production of $^{225}$Ac and $^{223}$Ra by Irradiation of Th with Accelerated Protons," Radiochemistry, vol. 53, No. 1, pp. 73-80 (2011).
Graeme Melville, et al., "Cyclotron and linac production of Ac-225," Applied Radiation and Isotopes 67, pp. 549-555 (2009).
G. Lange, et al., "Die Darstellung von Strontium-90-freiem Yttrium-90 durch Electrolyse," J. Inorg. Nucl. Chem., vol. 7, pp. 146-154 (1957).

* cited by examiner

METHOD FOR PRODUCING AC-225 FROM RA-226

CROSS-REFERENCE TO RELATED PATENT APPLICATIONS

This application claims the benefit of a European Application No. EP 19212438.6, filed Nov. 29, 2019, the disclosure of which is hereby incorporated by reference in its entirety.

TECHNICAL FIELD

The embodiments of the present disclosure relate to a method for producing Ac-225 from Ra-226 wherein said Ra-226 is present as a liquid solution in a recipient, said Ra-226 being submitted to a photo-nuclear process wherein the Ra-226 (γ,n) is irradiated to produce Ra-225 which then decays into the Ac-225.

BACKGROUND

Such a method is known from WO 01/41154. According to the known method, a solution comprising Radium-226 is placed in a recipient, and a beam of electrons is then targeted at a converting material for producing photons. The photons are then targeted at the Radium-226 so that a photodisintegration reaction occurs and Ra-225 is formed, which decays into Ac-225. The obtained Ac-225 can then be collected by a wet chemical process by using an ion exchange column.

A drawback of the known method is that it requires a radiochemical manipulation for recycling the targeted Ra-226. Such a recycling is time consuming and involves a very risky process as Ra-226 is a highly radioactive substance.

SUMMARY

It is an object of the embodiments of the present disclosure to avoid the recycling process of the Ra-226 after the chemical separation of the Ac-225.

To this purpose, the method according to the embodiments of the present disclosure is characterized in that the formed Ac-225 is collected by an electrochemical precipitation of it on a cathode present in said recipient, said cathode being removed from said recipient after said precipitation occurred and brought into a hot cell environment where said Ac-225 is extracted from said cathode. Instead of transporting the irradiated Ra-226 target, only the cathode with the electrodeposited Ac-225 is removed from said recipient after said precipitation occurred and brought into a suitable hot cell environment where said Ac-225 is extracted from said cathode. Since the Ra-226 remains in the recipient and since only the cathode with the deposited Ac-225 is transported, a significantly smaller hot cell environment is required to harvest the Ac-225 from the cathode. The Ra-226 stays in the recipient ready for continuing the irradiation procedure without any recycling protocol having to be applied.

It should be noted that using an electrochemical precipitation of radionuclides on a cathode is as such known. The article "Die Darstellung von Strontium-90-freiem Yttrium-90 durch Electrolyse" of G. Lange, et al published in J. Inorg. Nucl. Chem. 4 (1956), pages 146-154 describes such an electrochemical precipitation for obtaining Y-90 starting from Sr-90. However, the starting conditions for the two processes are very much different. The half-life of Sr-90 is 28.79 years, while the half-life of Ra-226 is 1600 years. This means, that if there is the same activity of Sr and Ra in a solution, the physical amount of radium (the number of atoms) is 1600/28.79=55.57 times higher than that of strontium, i.e. the concentration of radium is 55.57 times higher than that of strontium if a solution is considered. Already for this reason, a skilled person dealing with obtaining Ac-225 from Ra-226 will not consider this art as being relevant. The problem that has been solved by the cited art dealing with the Sr-90/Y-90 generator is to have a selective separation process of Y-90 from a Sr-90/Y-90 solution with minimal amounts of chemicals used during the whole process so that Sr-90/Y-90 generators can be used in a hospital radio-pharmacy. The teaching of this document is not directed to the development of an isotope production process by irradiation, and the recycling of the Sr-90 source is not considered.

A first embodiment of the method according to the present disclosure is characterized in that said Ra-226 is irradiated with photons having an energy of at least 6.4 MeV generated as Bremsstrahlung from an e-beam having an energy higher than 6.4 MeV. In such a manner, an intensive beam of photons is generated so that a sufficient amount of Ac-225 can be formed.

A second embodiment of the method according to the present disclosure is characterized in that said Ac-225 extracted from said cathode is chemically purified so as to remove traces of coprecipitated Ra-226 and Ra-225.

The embodiments of the present disclosure will now be described in more details hereinafter, thereby also referring to the annexed drawings.

DETAILED DESCRIPTION OF THE DRAWINGS

The alpha emitting radionuclide Ac-225 and its daughter Bi-213 are successfully used in systemic Targeted Alpha Therapy (TAT), such as for example described in the article "Actinium in targeted alpha-particle therapeutic application" of Scheinberg D. A., McDevit R. and published in Curr Radiopharm. 2017; 211 (4), pages 306-320. A significant success has recently been achieved in the treatment of metastatic prostate cancer therapy using Ac-225. Consequently, this success induced a high demand for Ac-225. However, the current world-wide production of Ac-225 is far away to meet the demand of this important radionuclide.

Figure 1:
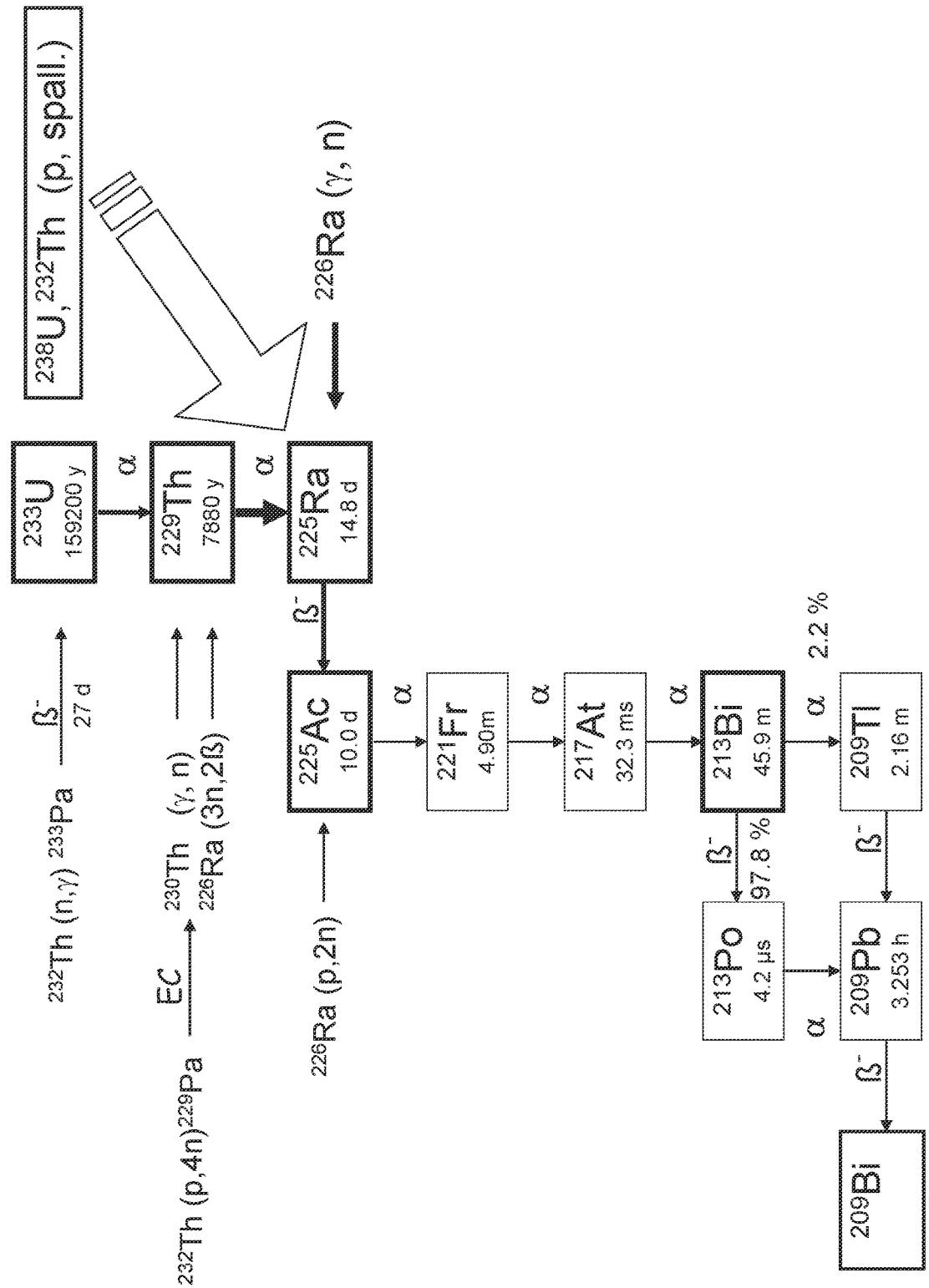
FIG. 1 represents an overview of the decay chain of U-233 and the different approaches for generating Ac-225.

FIG. 1 represents an overview of the decay chain of U-233 and the different approaches for generating Ac-225. There are three main strategies for production of Ac-225. The first being an indirect production of Ac-225 via the alpha-decay of Th-229. The second being an indirect production via the beta-decay of Ra-225 and the third being the direct production mode for Ac-225.

Most of the Ac-225 used so far has been separated from Th-229 that was obtained from the breeding process Th-232 (n,γ) Pa-233→U-233 in the cold war period. The available stock of Th-229 today is about 5 GBq located in Oakridge (USA) and around 1.7 GBq in Karlsruhe. Smaller quantities have been separated from U-233 in Obninsk (Russia). [Boll R. A., Malkemus D., Mirzadeh S., Production of actinium-225 for alpha particle mediated radioimmunotherapy, Appl. Radiat. Isot. 2005; 62: 667-679].

The reprocessing of the few tons of U-233 to separate the Th-229 that has been grown in in the meantime is technically complex due to the restrictions in handling fissile material. Only very small quantities of the U-233 material can be handled in one process batch and the quantity of extractable Th-229 is very low. Thus, the overall cost for such a process would be unacceptably high and the time scale unacceptably long.

The direct production technology of Ac-225 via high energy proton induced reaction has been developed in Troitzk (near Moscow). [B. L. Zhuikov, S. N. Kalmykov, S. V. Ermolaev, R. A. Aliev, V. M. Kokhanyuk, Matushko, I. G. Tananaev, B. F. Myasoedov, 2011, published in Radiokhimiya, 2011, Vol. 53, No. 1, pp. 66-72] and then transferred to the USA, where Ac-225 produced along this reaction in a collaboration between Brookhaven—Los Alamos—Oakridge national laboratories is offered to the users on a regular basis in a quantity of up to 1 Ci. The drawback of this process is that the nuclear reaction generates also Ac-227 in quantities that are not acceptable for direct use of the Ac-225 for therapeutic application.

A promising way to produce Ac-225 is the indirect production route via the photo-nuclear process of Ra-226($\gamma$, n) Ra-225→Ac-225. This process is described in WO 01/41154 and it has been experimentally demonstrated that Ac-225 in Ci-activities can be generated under realistic practical conditions. According to the known method a target of about 1 g Radium-226 is placed in a recipient and a beam of electrons is then targeted at a converting material for producing photons. The photons are targeted at the Radium-226 target so that a photodisintegration reaction occurs and Ra-225 is formed in the target. This primarily generated Ra-225, decays into Ac-225, the wanted product. The thus obtained Ac-225 can then be separated using a simple wet-chemical process using for instance an ion exchange column. Allen B. J. et. al compared the mentioned photo-nuclear process Ra-226 ($\gamma$,n) Ra-225 with the proton induced reaction at a small cyclotron Ra-226 (p,2n)-Ac-225 using Ra-226 as target material, concluding that the photo-nuclear reaction has great advantages, because of the possibility of using significantly larger quantities of Ra-226 and the possibility to perform the irradiation in solution (Melville G., Allen B. J. et. al, "Cyclotron and LINAC Production of Ac-225" Applied Radiat. Isot. 67 (2009) on pages 549-555).

The technological production scheme for making Ac-225 from Ra-226 along the photo-nuclear process or along the direct proton based Ra-226(p,2n)-process using cyclotrons is similar, i.e. preparing a small Ra-226 Target (~1 g) meeting all safety requirements, irradiation process and transportation of the irradiated target into a corresponding hot cell environment for processing. The only difference would be that in case of the photo-nuclear reaction one has to wait for about 8 days for growing in the wanted Ac-225 from the decay of the primarily formed Ra-225.

The radiochemical process including a dissolving and chromatographic separation, and purification of the final Ac-225 product is easy to perform. However thereafter the remaining Ra-226 solution needs to be recycled and converted into a new Ra-226 target for the next irradiation and production cycle. This recycling procedure, as part of each production process, is very risky because it involves handling of the highly radio-active material Ra-226. The recycling procedure is also time consuming.

According to the embodiments of the present disclosure, such a recycling process of the Ra-226 can be avoided by selectively extracting the obtained Ac-225 from the irradiated Ra-226 source thereby leaving the Ra-226 source in the recipient in which the photo-nuclear irradiation process took place. Instead of transporting the Ra-226 source or the complete irradiated Ra-226 solution to the place where the radiochemical separation process should take place, the embodiments of the present disclosure provide a method wherein only the Ac-225 obtained after irradiation is transported. The irradiation of the Ra-226 can be immediately continued after the separation of the Ac-225 without any further recycling operation. The separation process as such is based on a selective electrochemical precipitation of the Ac-225 at a cathode electrode, in particular made of Au, Ta, W, Nb, Rh, Pt or Ir or their alloy.

Figure 2:
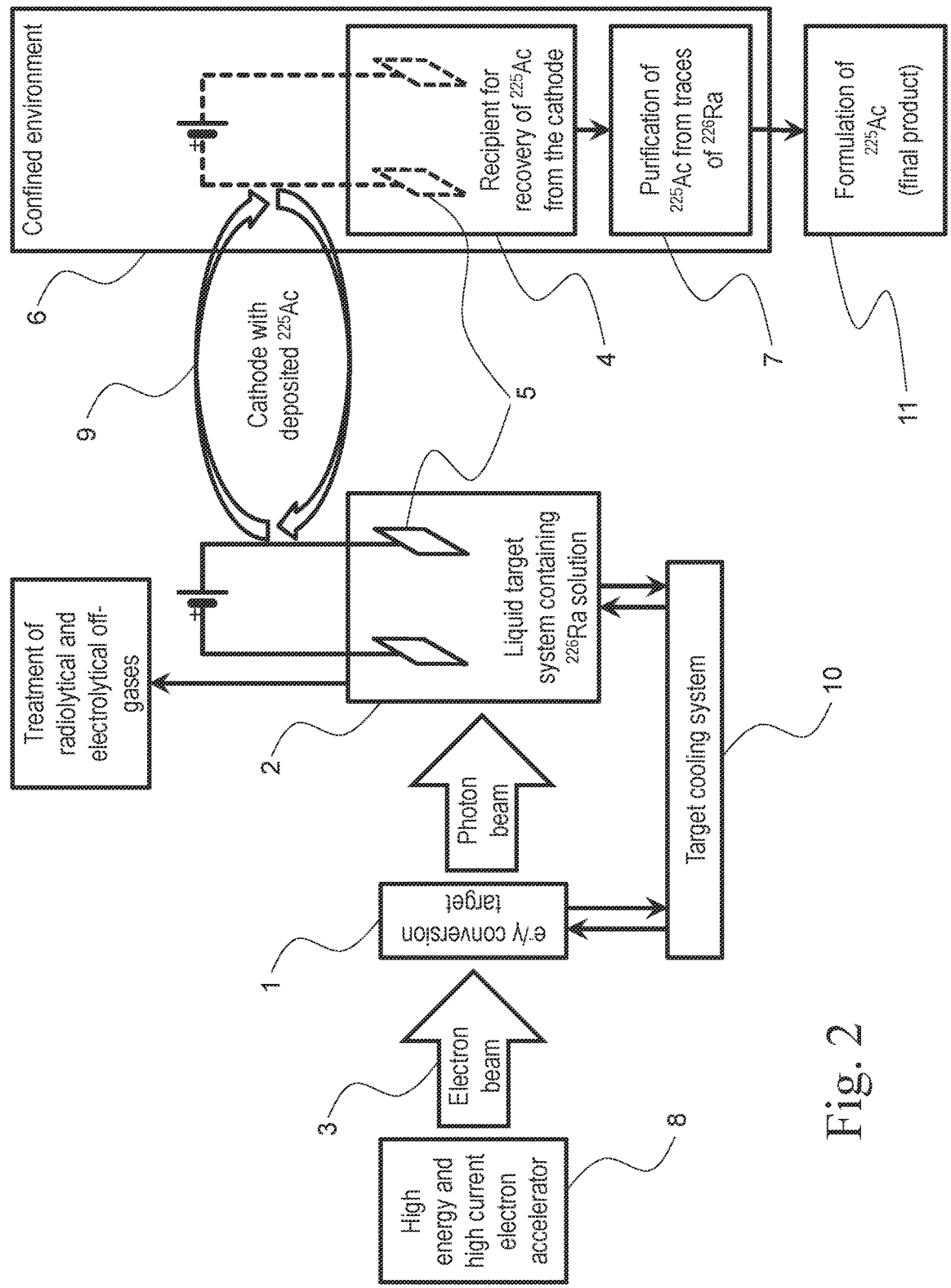
FIG. 2 shows a schematic example of a device which can be used for applying the method according to the embodiments of the present disclosure.

FIG. 2 schematically illustrates an example of a device for this electrochemical separation process. The device comprises a first recipient (2) in which the Ra-226 is present as a liquid solution. The first recipient forms a reaction vessel and is for example made of a radiation resistant material such as metal, quartz, glass or ceramics. The first recipient is irradiated by using a photo-nuclear source (1) on which a beam of electrons (3) is targeted. The photo-nuclear source (1), which is an electron-photon converter, comprises a converting material, such as for example Tungsten or Tantalum, which is targeted by the beam of electrons (3) for producing the photons, which will irradiate the Ra-226 solution present in the first recipient. The beam of electrons is for example produced by an electron accelerator (8). The first recipient is preferably irradiated with high energy photons having an energy of at least 6.4 MeV generated as bremsstrahlung from an intense e-beam beam having an energy higher than 6.4 MeV. For example, an electron beam having 18 MeV energy would generate photons of such energy distribution through bremsstrahlung, so that about 25% of photons would be suitable for Ac-225 production. Increasing the energy of the electron beam to 40 MeV would increase the fraction of photons suitable for Ac-225 production to 56%. Increasing the electron energy above 40 MeV will only slightly increase the yield of Ac-225, but will give rise to other competing nuclear reactions, e.g. ($\gamma$,2n) having a threshold photon energy at 11.3 MeV, ($\gamma$,3n) with threshold energy at 17.8 MeV and ($\gamma$,4n) with threshold energy at 23.0 MeV.

A cathode (5) is removably installed in the first recipient (2). The device further comprises a second recipient (4), which is separated from the first recipient. The cathode (5) can be removed from the first recipient and brought into the second recipient, as indicated by the arrows (9). The cathode transfer is arranged in a tight and shielded manner, avoiding a leakage of radio-active material. The cathode is preferably a Winkler electrode, a rod, a thin plate, or a wire. The recipient itself could form the anode. The irradiation goes through the anode and the electrical current between the anode and the cathode causes the Ac-225 to flow to the cathode.

Instead of using only one first recipient, it could also be possible to connect the first recipient (2) with a third recipient (not shown in the figure), in such a manner that the Ra-226 solution can circulate from the first to the third recipient. The third recipient is then preferably made of the same material as the first recipient. In the latter embodiment the cathode would then be placed in the third recipient during the irradiation.

The device preferably further comprises a cleaning station (7), separated from the first and second recipient. The cleaning station serves to remove impurities from the Ac-225, mainly co-precipitated micro-traces of the target material itself and the Ra-225 generated in the photo-nuclear reaction. The second recipient (4) and the cleaning station (7) are preferably housed in a confined environment (6) so as to limit considerably the risk of nuclear radiation to the outside environment.

In the device, the Ra-226 solution is submitted to the photo-nuclear irradiation for forming Ra-225. The Ac-225 is then formed by the radioactive decay of Ra-225 and collected by the electrochemical precipitation on the cathode (5) present in the first recipient. The cathode is removed from the first recipient after the electro-precipitation occurred and brought into the second recipient (4) located away from the first recipient. In this hot cell environment formed by the second recipient, the separation of the collected Ac-225 from the cathode takes place. This collecting process is executed mainly without disturbing the main Ra-226 activity used in the irradiation process. The original Ra-226 target solution remains within the first recipient and irradiation can continue without further treatment of the Ra-226.

A great advantage of the embodiments of the present disclosure is the fact that the large quantity of Ra-226 is never handled in the second recipient which forms the environment used for separation of the Ac-225. This means that the radiation safety requirements related to transporting and handling of the Ac-225 containing cathode are much easier fulfilled, compared to handling large quantities of Ra-226. Moreover, the radiation safety issues related to the construction and operation of the hot cell in which the cathode with the precipitated Ac-225 is processed are also significantly milder, since only trace amounts of Ra-226 are present in the hot cell.

From experimental data for the electrochemical separation process one can conclude that:
- The higher the current density at the cathode surface, the faster the deposition of Ac-225 will take place.
- The lower the pH the faster the deposition speed. A pH below 6 and more particularly in the range of 1-4 being preferred.
- The lower the current density, the lower will be the change of the pH of the solution. An optimal current density being in the region of 20-300 mA/cm$^2$.
- The smaller the ratio between sample volume and cathode surface the higher the deposition yield will be.
- The higher the current density, the more the temperature of the solution will increase. An increased temperature has a significant influence on the deposition speed.

The Ra-226 present in the first recipient is preferably irradiated in a nitrate (HNO$_3$) solution. The volume of the target solution can vary between 50 ml up to several liters. The volume depends on the quantity of Ra-226 target material which shall be irradiated. The concentration of the Ra-226 in the nitrate solution can be up to 0.2 M corresponding to about 50 g of Ra-226 per liter. The pH of the nitrate solution is preferably below 6 and more preferably between 1 and 4, preferably adjusted with HNO$_3$. During the electrochemical milking process the pH might slightly increase. The alteration of the pH does not have an influence on the electrochemical separation efficiency as long as the pH is below 6 and more preferably in the 1 to 4 range. Nevertheless, it is preferred to control and correct the pH from time to time, for instance after 10 to 20 production runs, by adding adequate small volumes of 1 M HNO$_3$. By doing so, the electrochemical precipitation rate will be maintained at its maximum value.

Generally, two electrodes are present in the first recipient, where the electrochemical precipitation is performed. The first electrode is functioning as the anode and the second electrode as the cathode (5). If the recipient is made from a noble metal, for instance Pt or Ir or their alloy, one can use the recipient as the anode. In this case only the cathode is placed inside the first recipient. The dimension of the cathode for the electrochemical precipitation determines mainly the speed of the Ac-225 deposition. For determining the cathode surface, one needs to consider the volume of the processed solution.

During the electrochemical process the temperature of the processed solution increases. In order to avoid significant evaporation of the Ra-226 solution during irradiation and electrolysis a cooling of the solution is preferred. This is for example realised by a cooling station (10) provided for cooling the first recipient (2) and the photo-nuclear source (1). A thermostat approach is preferred to stabilize the temperature at a defined level, preferably 30° C. Under these conditions the time for >90% electrochemical precipitation would be increased, however due to the half-life of the Ac-225 there is no need for tight time limits and one to even a few hours of electrochemical processing is acceptable.

Three different modes for applying the method according to the embodiments of the present disclosure can be applied:
a. an interrupted (batch-wise) production mode
b. a semi-online production mode
c. a continuous production mode.

In the interrupted (batch-wise) mode during the irradiation of the Ra-226 the latter is partially converted into Ra-225. After about two weeks of irradiation about 50% of the theoretical saturation activity of Ra-225 is reached. In the meantime, the obtained Ra-225 decays to Ac-225, reaching the maximum after about 8 days. Thereafter the electrochemical precipitation is executed which lasts for a few hours. The cathode with precipitated Ac-225 is subsequently transferred to the second recipient, where the Ac-225 is collected from the cathode. The cathode is thereafter returned to the first recipient. It could also be considered to use two or even a plurality of recipients and irradiate them alternately with the same irradiation source. After the end of an irradiation cycle during which one of the recipients was irradiated, the electron beam could be switched to irradiate the other recipient. Under any circumstances one can harvest weekly one batch of Ac-225. The time intervals for irradiation and decay period can be altered with high flexibility according the practical needs.

In the semi-online mode irradiation is only interrupted during the short period of the milking process. After longer continuous irradiation a steady state condition is reached, meaning synthesis and decay of Ra-225 are practically in equilibrium. The e-beam is switched off and the electrochemical precipitation process starts immediately, extracting that fraction of Ac-225, that has been generated from the decay of Ra-225 during irradiation. After the cathode has been transferred for the processing of the Ac-225 the irradiation continues independent of the still existing activity of Ra-225. In this operation mode one can extract weekly a new batch of Ac-225.

In the continuous operation mode, it may well be that one can execute the milking process even under irradiation condition. This option can be proved only under practical conditions.

The electroplated Ac-225 can be dissolved from the cathode with about 1 M HNO$_3$-solution or as option electrochemically switching the electrode as anode in a weak acid solution. The transferred cathode will contain some small quantities of Ra-226 in the order of 50 μL of the original target solution. Any known process for Ac-225 purification can be applied, preferably chromatographic separation processes. The purified Ac-225 is then stored (11) in a suitable containment.

During irradiation, the acidic Ra-226 solution undergoes a certain radiolytical destruction whereby $H_2$ and $O_2$ is formed. Further, from the decay of Ra-226 one has to consider the radioactive gas Rn-222. The target solution should therefore preferably be purged with a slow inert gas stream, such as for example He, at least during electro deposition of the Ac-225. This means that one has to deal with some water vapor in the off-gas stream. The total gas volume that needs to be treated is relatively small and is estimated to be around 0.5 l/h. The treatment of the off gas can be done in the following way: the off gas is passing an adequately efficient chilling column installed in refluxing mode where the condensed liquid is returned quantitatively back into the first recipient. The cooling temperature shall be between 1 and 10° C. After passing the chiller the off gas is passing a mole sieve cartouche for trapping the last traces of moisture. Then, the off gas is passing a charcoal cartouche chilled to a temperature below 15° C. This charcoal cartouche traps the Rn-222 practically quantitatively. For safety reasons a cryogenic trap is preferably included to extract last potential traces of Rn-222 from the off gas. The off gas from the separation and purification process carried out separately from the target station will be treated in the same way. The concentration of the released $H_2$ and $O_2$ is below the explosion level, thus removal of these gases from the off-gas stream is not required.

The invention claimed is:

1. A method for producing Ac-225 from Ra-226, the method comprising:
   submitting Ra-226 to a photo-nuclear process, wherein the Ra-226 comprises a liquid solution in a recipient;
   irradiating the Ra-226 to produce Ra-225, wherein the Ra-225 decays into Ac-225 upon irradiation of the Ra-226;
   collecting an electrochemical precipitation of the Ac-225 on a cathode in the recipient;
   removing the cathode from the recipient after the electrochemical precipitation of the Ac-225;
   transferring the cathode to a hot cell environment; and
   extracting the Ac-225 from the cathode in the hot cell environment.

2. The method as claimed in claim 1, wherein the Ra-226 is irradiated with photons having an energy of at least 6.4 MeV, and wherein the energy is generated as Bremsstrahlung from an e-beam having an energy higher than 6.4 MeV.

3. The method as claimed in claim 1, wherein the cathode is made of a chemically inert metal.

4. The method as claimed in claim 1, wherein the Ac-225 extracted from the cathode is chemically purified to remove traces of coprecipitated Ra-226 and Ra-225.

5. The method as claimed in claim 1, wherein the liquid solution comprises a nitric acid ($HNO_3$) solution with a pH below 6.

6. The method as claimed in claim 1, further comprising, prior to collecting the electrochemical precipitation of the Ac-225, performing the electrochemical precipitation of the Ac-225 using a plurality of separate recipients.

7. The method as claimed in claim 1, further comprising:
   performing the electrochemical precipitation of the Ac-225 batch-wise; and
   interrupting the irradiation when the cathode is transferred to the hot cell environment.

8. The method as claimed in claim 1, wherein the liquid solution is purged with an inert gas stream.

9. The method as claimed in claim 8, wherein the inert gas stream comprises a helium (He) stream.

10. The method as claimed in claim 3, wherein the chemically inert metal comprises gold (Au), tantalum (Ta), tungsten (W), niobium (Nb), rhodium (Rh), platinum (Pt), iridium (Ir), or alloys thereof.

11. The method as claimed in claim 5, wherein the $HNO_3$ solution comprises a pH between 1 and 4.

\* \* \* \* \*